US009381255B2

(12) United States Patent
Rubin et al.

(10) Patent No.: US 9,381,255 B2
(45) Date of Patent: Jul. 5, 2016

(54) FORMULATIONS COMPRISING T3 NANOPARTICLES

(71) Applicants: Avant Garde Therapeutics and Technologies LLC, Suffern, NY (US); Diane Rubin, Suffern, NY (US)

(72) Inventors: Leo Rubin, Suffern, NY (US); Shaker Mousa, Wynantskill, NY (US)

(73) Assignee: AVANT GARDE THERAPEUTICS AND TECHNOLOGIES LLC, Suffern, NY (US)

( * ) Notice: Subject to any disclaimer, the term of this patent is extended or adjusted under 35 U.S.C. 154(b) by 0 days.

(21) Appl. No.: 13/777,489

(22) Filed: Feb. 26, 2013

(65) Prior Publication Data
US 2013/0243868 A1    Sep. 19, 2013

Related U.S. Application Data

(63) Continuation of application No. 12/796,273, filed on Jun. 8, 2010, now Pat. No. 8,404,281.

(60) Provisional application No. 61/184,903, filed on Jun. 8, 2009, provisional application No. 61/248,127, filed on Oct. 2, 2009.

(51) Int. Cl.
*A61K 31/198*    (2006.01)
*B82Y 5/00*    (2011.01)
*C07D 303/38*    (2006.01)
*C07D 303/40*    (2006.01)
(Continued)

(52) U.S. Cl.
CPC ........... *A61K 47/4823* (2013.01); *A61K 9/5153* (2013.01); *A61K 9/5161* (2013.01); *A61K 31/198* (2013.01); *A61K 47/482* (2013.01); *A61K 47/48176* (2013.01); *A61K 47/48907* (2013.01); *B82Y 5/00* (2013.01); *C07D 303/38* (2013.01); *C07D 303/40* (2013.01)

(58) Field of Classification Search
CPC ........... A61K 31/198; A61K 47/48176; A61K 47/482; A61K 47/4823; A61K 47/48907; A61K 9/5153; A61K 9/5161; B82Y 5/00; C07D 303/38; C07D 303/40
See application file for complete search history.

(56) References Cited

U.S. PATENT DOCUMENTS 3,689,669 A * 9/1972 Prange et al. ................. 514/567
4,673,691 A * 6/1987 Bachynsky ................... 514/567
6,242,099 B1   6/2001 Grandmontagne et al.
(Continued)

FOREIGN PATENT DOCUMENTS

WO    WO 2007/086651    8/2007
WO    WO 2008/051291    5/2008
(Continued)

OTHER PUBLICATIONS

International Search Report for International Application No. PCT/US2011/040704 mailed Oct. 27, 2011.
(Continued)

*Primary Examiner* — Ernst V Arnold
(74) *Attorney, Agent, or Firm* — Hoxie & Associates LLC

(57) ABSTRACT

Nanoparticles comprising T3 and their use in treating, e.g., cardiac conditions, for example cardiac arrest, are provided. Such nanoparticles provide improved delivery of T3 and allow for acute treatment and optionally for sustained release of T3 in a patient.

15 Claims, 18 Drawing Sheets

Source: M.N.V. Ravi Kumar et al. / Biomaterials 25 (2004) 1771-1777

(51) Int. Cl.
*A61K 47/48* (2006.01)
*A61K 9/51* (2006.01)

(56) References Cited

U.S. PATENT DOCUMENTS

| | | |
|---|---|---|
| 7,604,795 B1 | 10/2009 | Sung et al. |
| 8,071,134 B2 | 12/2011 | Mousa et al. |
| 8,404,281 B2 | 3/2013 | Rubin et al. |
| 2004/0156904 A1 | 8/2004 | Saltman et al. |
| 2005/0118109 A1 | 6/2005 | Block et al. |
| 2005/0124862 A1 | 6/2005 | Mousa et al. |
| 2006/0141046 A1 | 6/2006 | Cattaneo |
| 2007/0068824 A1 | 3/2007 | Payne et al. |
| 2008/0200430 A1 | 8/2008 | Bitterman et al. |
| 2008/0200434 A1 | 8/2008 | Daniloff |
| 2008/0213354 A1 | 9/2008 | Sung et al. |
| 2008/0287341 A1 | 11/2008 | Chen |
| 2009/0022806 A1 | 1/2009 | Mousa et al. |
| 2010/0161038 A9 | 6/2010 | Rubin et al. |
| 2011/0158901 A1 | 6/2011 | Santra |
| 2013/0337053 A1 | 12/2013 | Rubin et al. |
| 2013/0338072 A1 | 12/2013 | Rubin et al. |
| 2014/0322341 A1 | 10/2014 | Rubin et al. |
| 2014/0328933 A1 | 11/2014 | Rubin et al. |

FOREIGN PATENT DOCUMENTS

| | | |
|---|---|---|
| WO | WO 2011/159899 | 12/2011 |
| WO | WO 2012/170017 | 12/2012 |
| WO | WO 03/103743 | 12/2013 |

OTHER PUBLICATIONS

International Search Report and Written Opinion of the International Searching Authority [US] for International Application No. PCT/US2011/039553 dated Jan. 6, 2012.
Kumari et al., "Biodegradable polymeric nanoparticles based drug delivery systems", Colloids and Surfaces B: Biointerfaces 75:1-18 (2010).
Pochanavanich et al., "Fungal chitosan production and its characterization", Letters in Appl. Microbiol. 35:17-21 (2002).
Jeevanandam, "Triiodothyronine: Spectrum of Use in Heart Transplantation," Thyroid 7:139-145 (1997).
International Search Report for International Application No. PCT/US2011/039553 mailed Dec. 13, 2012.

* cited by examiner

Figure 5A

Date: 04.10.2009

| Samples | PLGA (ratio) | Chitosan | PVA | Sonication time (min) | Stirring time | pH value | Particle size(nm) | Distribution | Zeta potential | Meet Quality criteria? |
|---|---|---|---|---|---|---|---|---|---|---|
| Chitosan-pva-1 | 40mg | 15mg | 50mg | - | overnight | 5.0* | 782 | multimodal | +50.0mV | |
| Chitosan-pva-2 | 20mg | 15mg | 50mg | 2+2+2 | >4h | 5.3* | 166 | unimodal | +35.6mV | Y |
| Chitosan-pva-3 | 75:25 40mg | 15mg | 100mg | 1+2 | >4h | 5.0* | 187 | unimodal | +35.9mV | Y |
| Chitosan-pva-4 | 40mg | 30mg | 100mg | 2+2 | >4h | 5.7* / 10.5-11** / 7.2*** | 200 / 150 / 296 | unimodal / multimodal / multimodal | +42.3mV / -1.11mV / +3.11mV | Y |
| Chitosan-pva-5 | 40mg | 30mg | 100mg | 2+2 | >4h | 5.0* | 190 | unimodal | +41.8mV | Y |
| Chitosan-pva-6 | 65:35 40mg | 30mg | 100mg | 2+2 | >4h | 5.0* | 185 | unimodal | +35.8mV | Y |
| Chitosan-pva-7 | 75:25 20mg + 65:35 60mg | 30mg | 100mg | 2+2 | overnight | 5.2* | 237 | unimodal | +40.6mV | Y |
| Chitosan-pva-8 | 65:35 100mg | 30mg | 100mg | 2+2 | overnight | 5.3* | 248 | unimodal | +43.4mV | Y |

* chitosan solution (0.1N HCL, pH 1) was adjusted to pH 5~6 by adding NaOH solution (0.1N) before reaction and the pH value does not change after preparation of nanoparticles.
** adjusted by NaOH solution (0.1N)
*** adjusted by HCl solution (0.01N)

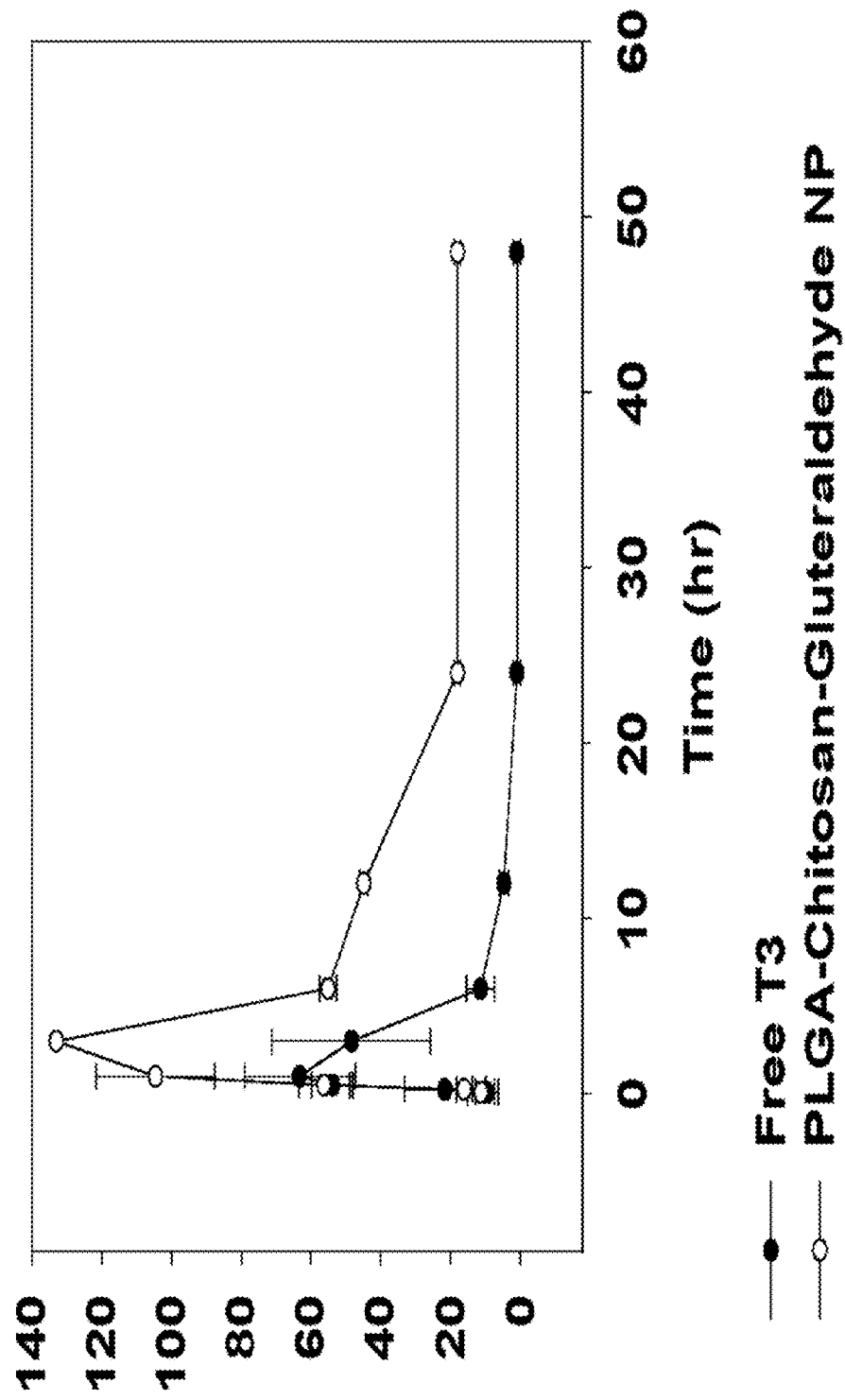

FORMULATIONS COMPRISING T3 NANOPARTICLES

This application claims the benefit of U.S. Provisional Application 61/184,903 filed Jun. 8, 2009, and U.S. Provisional Application 61/248,127, filed Oct. 2, 2009, the contents of each of which are incorporated herein by reference.

TECHNICAL FIELD

The field relates to nanoparticles comprising triiodothyronine (T3), and to their use in treatment of cardiac conditions, particularly cardiac arrest and acute heart failure.

BACKGROUND OF THE INVENTION

Cardiac arrest refers to a state where the heart of the patient has stopped beating effectively and is no longer functioning to pump blood around the body. It is often caused by myocardial infarction. If treated promptly, cardiac arrest may sometimes reversed by cardiopulmonary resuscitation (CPR) and defibrillation. Drugs to treat cardiac arrest include epinephrine, which stimulates the heart muscle and also augments pressure in the aorta, which drives coronary perfusion. Whether epinephrine significantly improves overall survival is controversial, however, because while it may improve the chances for resuscitation, it may also cause arrhythmias and strain on the heart which increase the risk of problems in the post-resuscitation phase.

Other forms of acute cardiac insufficiency include acute heart failure and cardiogenic shock. Acute heart failure is a critical condition that is commonly seen in patients with chronic heart disease. During acute heart failure, the ability of the heart to pump blood from the lung circulation into the peripheral circulation is impaired. Cardiogenic shock is a form of shock resulting from an inadequate circulation of blood due to primary failure of the ventricles of the heart to function effectively.

Triiodothyronine, also known as T3, is a thyroid hormone. Thyroid-stimulating hormone (TSH) activates the production of thyroxine (T4) and T3. T4 is converted to T3 by deiodination. T3 affects a variety of body processes, including body temperature, growth, and heart rate. T3 has important effects on cardiac tissue. Thyroid hormones, notably T3, modulate ventricular function via genomic and non-genomic mechanisms. Cardiac stress events (cardiac arrest, myocardial infarction, etc.) are associated with steep reductions in serum T3 levels. Post resuscitation T3 level correlates highly with survival rate. T3 additionally has cardiostimulatory properties: it increases the cardiac output by increasing the heart rate and force of contraction. Overall, there is reason to believe that early bolus T3 injection could increase chances of resuscitating cardiac arrest victims, and that elevating T3 serum concentration could increase prospects of survival to hospital discharge.

T3 is not currently approved for this indication, however, and current formulations of T3 are not well suited for this purpose. Triostat® requires refrigeration, making it somewhat impractical for emergency use. Also, the concentration is low for what is needed to treat cardiac arrest. T3-albumin formulation have been described but are difficult to make, and like Triostat®, have poor stability and are poorly suited for quick administration in an emergency setting.

SUMMARY OF THE INVENTION

The invention provides T3 nanoparticles, wherein the T3 is encapsulated or immobilized by a bioabsorbable polymer, for example, having any of the following characteristics a. Wherein the polymer comprises chitosan.

b. Wherein the polymer comprises poly(lactic-co-glycolic acid) (PLGA) or polylactic acid (PLA), e.g., PLGA having 50/50 co-polymerization of D,L-lactic acid and glycolic acid.

c. Wherein the polymer comprises chitosan crosslinked using glutaraldehyde.

d. Wherein the polymer comprises chitosan linked to bile acids.

e. Wherein the polymer comprises chitosan linked to PLGA, e.g., using glutaraldehyde as crosslinker.

f. Any of the foregoing wherein the nanoparticles have an average diameter of 50-1000 nm, e.g., 100-500 nm or 50-250 nm.

g. Any of the foregoing wherein the nanoparticles have a zeta potential of 10-100 mV.

h. Any of the foregoing wherein the nanoparticle comprises a second pharmacologically active ingredient.

In one embodiment, the T3 is covalently linked to the bioabsorbable polymer, for example via the hydroxy on the phenyl moiety. Such compositions can be formed using activated T3 which is activated at the phenolic hydroxy with a suitable linker and protected at the amino moiety. For example, in one embodiment, amino-protected T3 is formed using the synthesis as shown in FIG. 9. The amino-protected T3 is then linked to the nanoparticle, for example via the phenolic hydroxy, e.g. by using an activated linker group, for example a moiety capable of coupling to an amine group on the bioabsorbable polymer, for example the amino moieties on chitosan.

In one embodiment, therefore, the invention provides activated T3 which is substituted on the phenolic hydroxy group with an epoxide moiety of formula [CH2-O—CH]—[CH2]$_n$— and which is amino protected. For example, the invention provides a compound of formula 1:

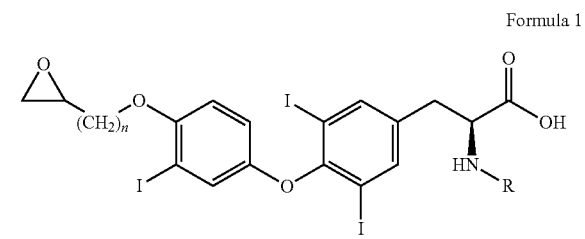

Formula 1 wherein n is an integer selected from 1 through 5, and R is an amino protecting group, e.g., butoxycarbonyl (BOC).

The T3 may thus be activated, for example using an epoxyalkyl of formula [CH2-O—CH]—[CH2]$_n$-X wherein n=1-5 and X is halogen, e.g. bromine, e.g. according to a synthesis as shown in FIG. 10. The resulting compound is then, if necessary, selectively deprotected to release the carboxy moiety, for example,

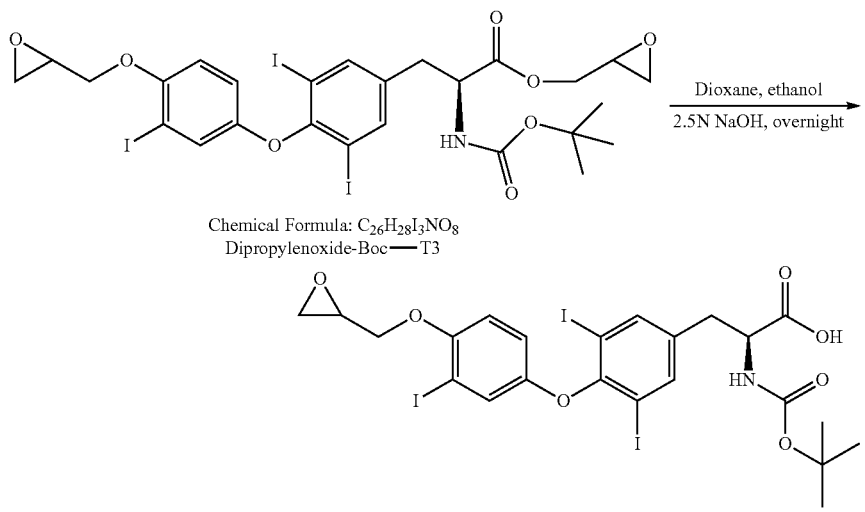

Chemical Formula: $C_{26}H_{28}I_3NO_8$
Dipropylenoxide-Boc—T3 to provide T3 which is activated at the phenolic hydroxy (here, with propylene oxide) and amino-protected (here, with BOC).

The activated T3 is then attached to the bioabsorbable polymer, for example, T3 having an epoxy linker moiety and an amino-protecting group is reacted with a bioabsorbable polymer having amino groups, then deprotected to provide a nanoparticle covalently linked to T3, e.g., as shown in FIG. 11. This reaction may be carried out in the presence of a stabilizer, such as polyvinyl alcohol, e.g. PVA 1% w/v, in an appropriate solvent, for example dimethylsulfoxide, e.g. DMSO (0.1% v/v) and acetic acid (0.1% v/v), which solvents are removed afterwards by dialysis. The number of T3 moieties attached to the nanoparticle may vary based on the reaction conditions and amount of reactant used, but if these conditions are kept constant, the distribution of variation will be low. Typically, the nanoparticle will comprise 20-200 T3 moieties, e.g., about 50 per nanoparticle. The amount of T3 in a batch can be assayed, e.g., as described below, by separating the nanoparticles by filtration or centrifugation, weighing, degrading the T3 nanoparticle in strong base, and measuring by HPLC.

The overall scheme may be for example as shown in FIG. 12.

In one example, the T3 nanoparticles are made from T3 and the following components:

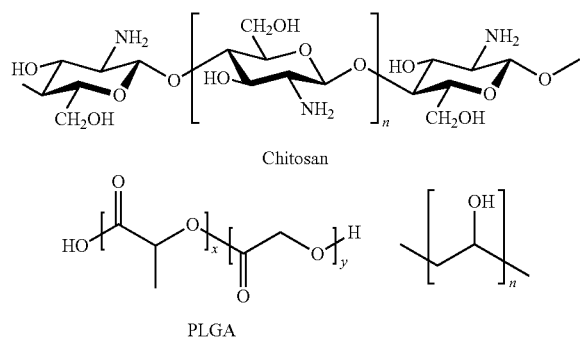

PVA (stabilizer). In one example, the nanoparticles have these components in approximately the following amounts:

| Components of the formulation | Approx Amount (% w/w) in the nanoformulation | Role in the formulation |
|---|---|---|
| Chitosan | 50-70%, e.g. 60% | Component of the nanocarrier |
| PLGA | 20-30%, e.g. 25% | Component of the nanocarrier |
| T3 | 10-20%, e.g. 15% | Active ingredient (chemically conjugated to the nanoparticles) |

The contents of the nanoparticles are confirmed using, e.g. HPLC and LC/MS. The nanoparticle formulations may be sterilized using conventional means, e.g., filtration, gamma radiation.

In one embodiment, the invention provides a method for treating a cardiac condition, e.g. cardiac arrest, cardiac arrhymia, or cardiac insufficiency, comprising administering an effective amount of a T3-nanoparticle to a patient in need thereof, wherein the T3-nanoparticle comprises a bioabsorbable polymer, for example as described above.

In a specific example of the method, the T3-nanoparticle administered comprises a chitosan-PLGA nanoparticles encapsulating T3.

In another example, the T3-nanoparticle administered comprises chitosan nanoparticles encapsulating T3 with glutaraldehyde as a cross linker. Other cross-linkers may be used. In yet another example, the T3-nanoparticle administered comprises chitosan-PLGA nanoparticles encapsulating T3 alone. Such examples of T3 nanoparticles may utilize a process that includes gelation/conjugation of preformed biodegradable polymers.

In yet another example, the T3-nanoparticle administered includes chitosan-PLGA nanoparticles immobilizing T3. Alternatively, the T3-nanoparticles administered comprises chitosan-PLGA nanoparticles immobilizing T3 as well as chitosan-PLGA nanoparticles encapsulating T3.

In another example, the T3-nanoparticle comprises T3 covalently linked to chitosan or chitosan-PLGA nanoparticles.

BRIEF DESCRIPTION OF THE FIGURES

FIGS. 2, 2A and 2B shows an example of a flowchart of PLGA-Chitosan nanoparticles encapsulating T3.

FIGS. 5A and 5B shows various measurements for T3-nanoparticles.

FIG. 8A shows one example of blood levels of T3 using T3-nanoparticles and T3 alone in mice.

DETAILED DESCRIPTION

The examples and drawings provided in the detailed description are merely examples, which should not be used to limit the scope of the claims in any claim construction or interpretation.

The methods using the T3 nanoparticles may be use to treat acute cardiac insufficiency. Examples of cardiac conditions that may be treated include cardiac arrest, cardiogenic shock, and acute heart failure.

For example, while not bound by theory, it is believed that delivery of T3-nanoparticles may act rapidly and directly increase the effective mechanical contraction of the heart, decrease systemic vascular resistance, and increase heart rate.

In one embodiment, the particles provide a sustained release which allows the T3 to affect gene expression. In another embodiment, the T3 is covalently linked to the bioabsorbable polymer, which reduces the genomic effect and enhances the effect on the integrin receptor.

The T3 nanoparticles of the invention may be administered in conjunction with, or adjunctive to, the normal standard of care for cardiac arrest, e.g., cardiopulmonary resuscitation, defibrillation, and epinephrine. They may be administered shortly after the cardiac arrest, and optionally later, e.g., 8-24 hours later, to preserve cardiac function.

Various methods of synthesizing T3-nanoparticles are provided. For example, a single emulsion process may produce chitosan-PLGA nanoparticles encapsulating T3. In yet another example, a process involving gelation/conjugation of preformed biodegradable polymers produces 1) chitosan nanoparticles encapsulating T3 with and without glutaraldehyde as a cross-linker; or 2) chitosan-PLGA nanoparticles encapsulating T3. Other cross-linkers may be used.

In yet another example, a process involving chemical bonding of T3 on the surface of chitosan-PLGA nanoparticles produces 1) chitosan-PLGA nanoparticles immobilizing T3 or 2) chitosan-PLGA nanoparticles immobilizing T3 and additionally including chitosan-PLGA nanoparticles encapsulating T3.

Figure 1:
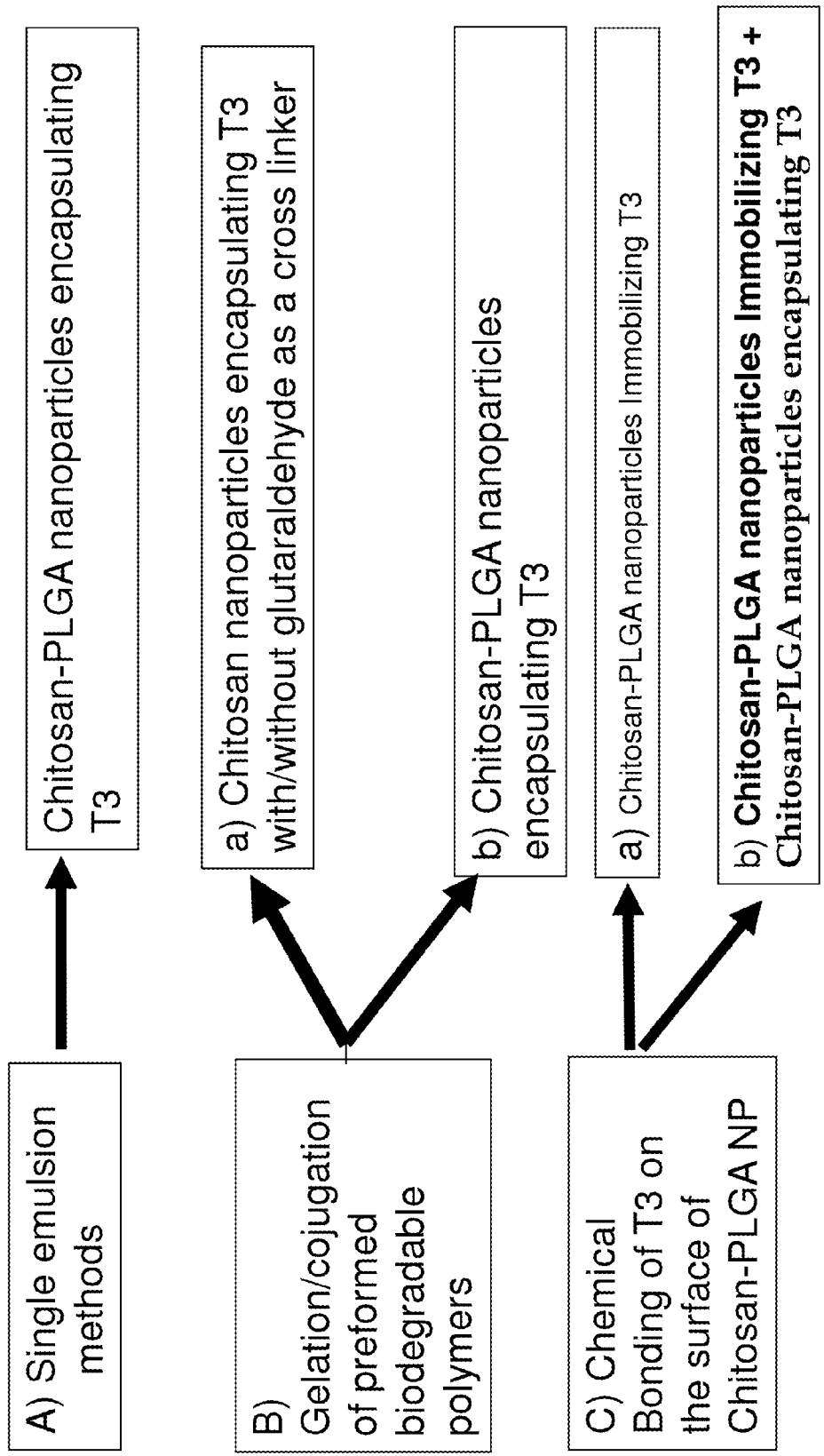
FIG. 1 depicts a schematic flowchart of various methods of synthesizing T3-nanoparticles.
Figure 2A:
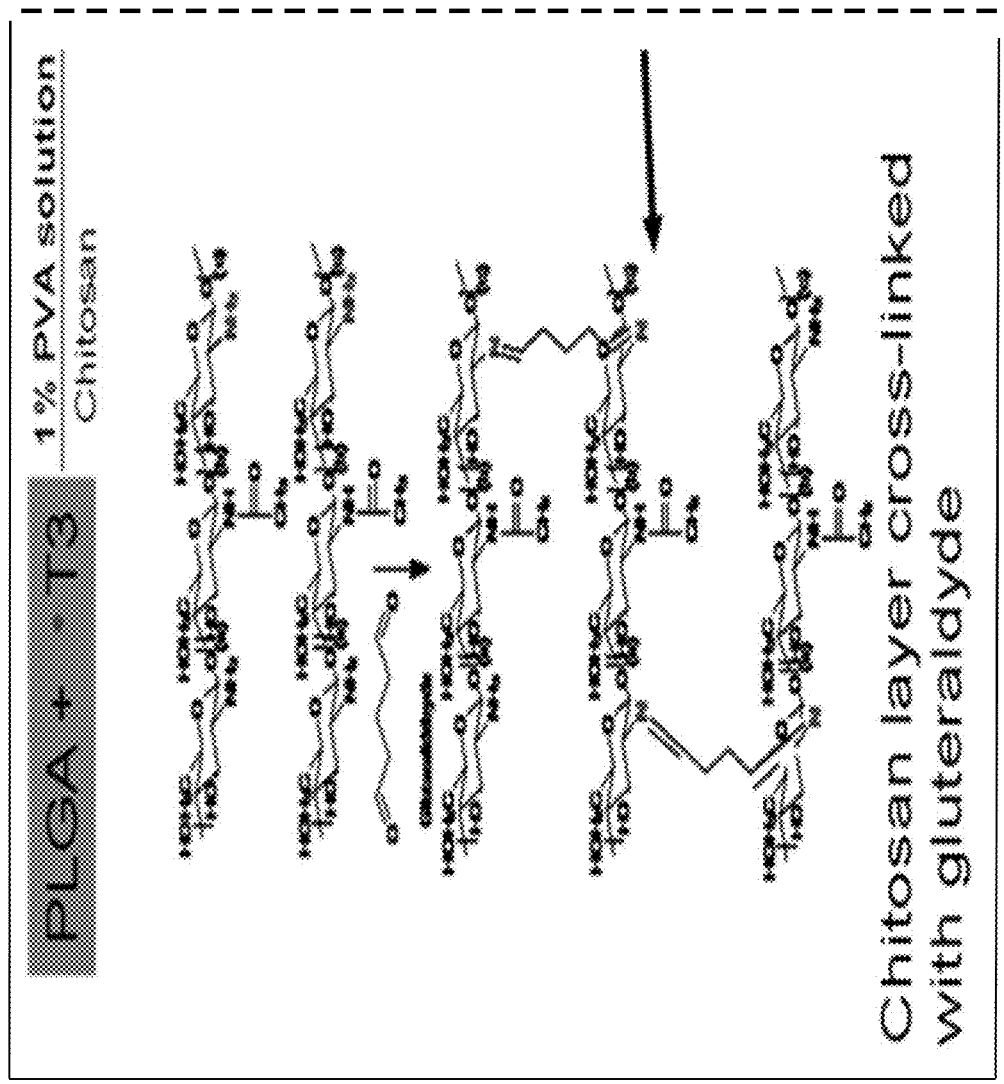
Figure 2B:
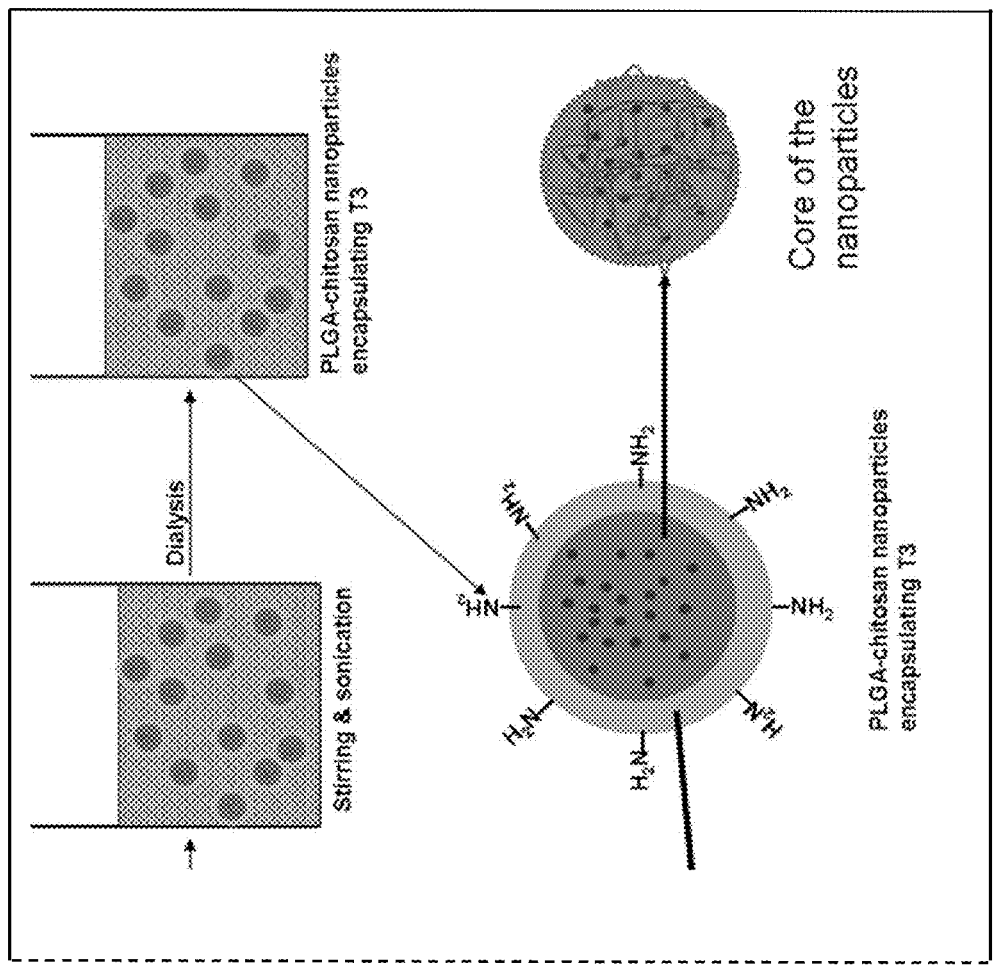

In FIG. 2, a flowchart shows an example of synthesis of PLGA-Chitosan nanoparticles encapsulating T3. In this example, PLGA and T3 are first immersed in a 1% PVA solution and chitosan. They are then stirred and sonicated. Then a dialysis step is performed. After a dialysis step occurs, PLGA-chitosan nanoparticles encapsulating T3 are produced. Then in the final step, the nanoparticles may then have a chitosan layer cross-linked with glutaraldehyde. Other cross-linkers may be used.

Figure 3A:
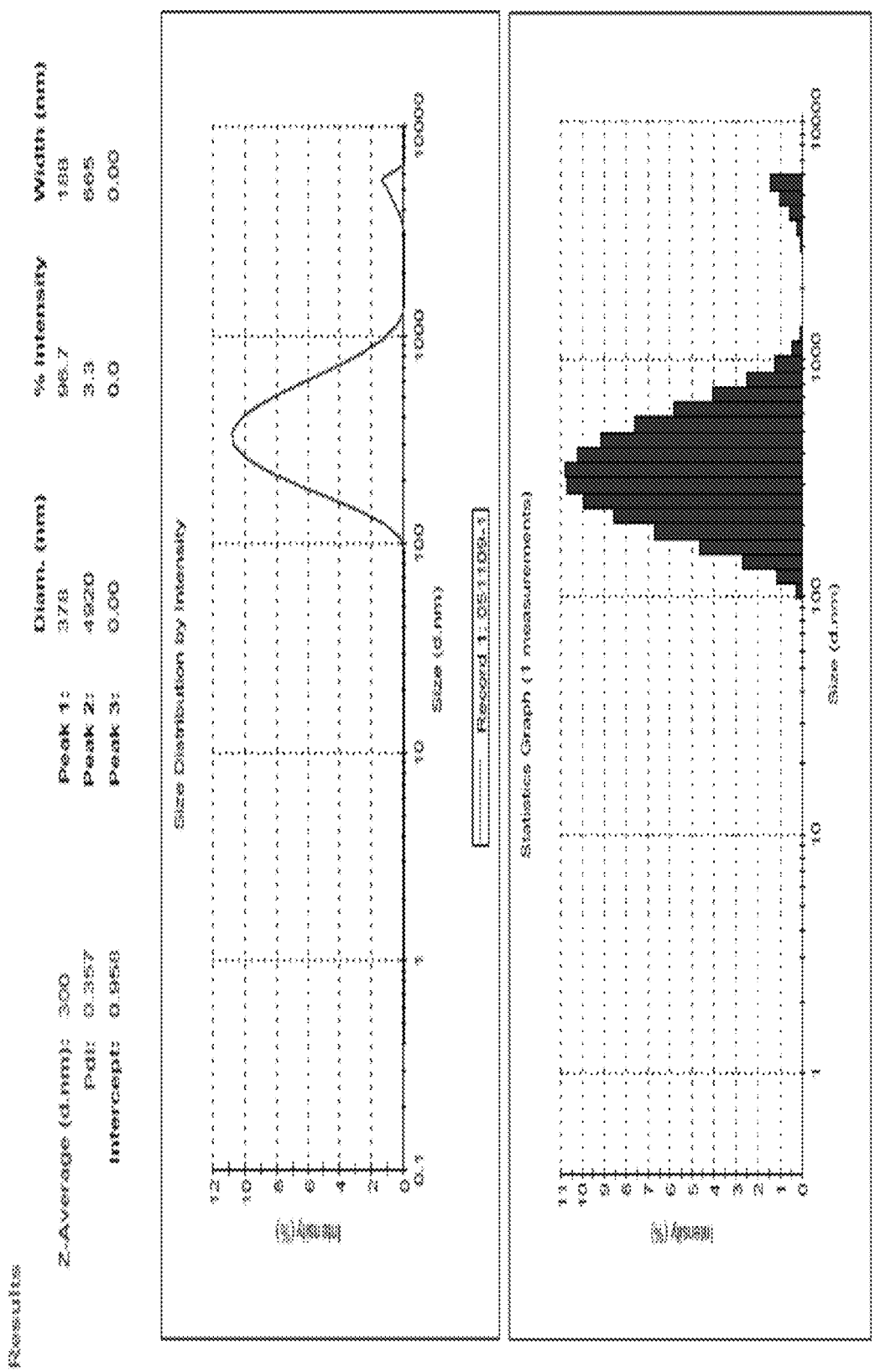
FIGS. 3A and 3B show a size measurement of T3 encapsulated PLGA-nanoparticles with and without a cross-linker.
Figure 3B:
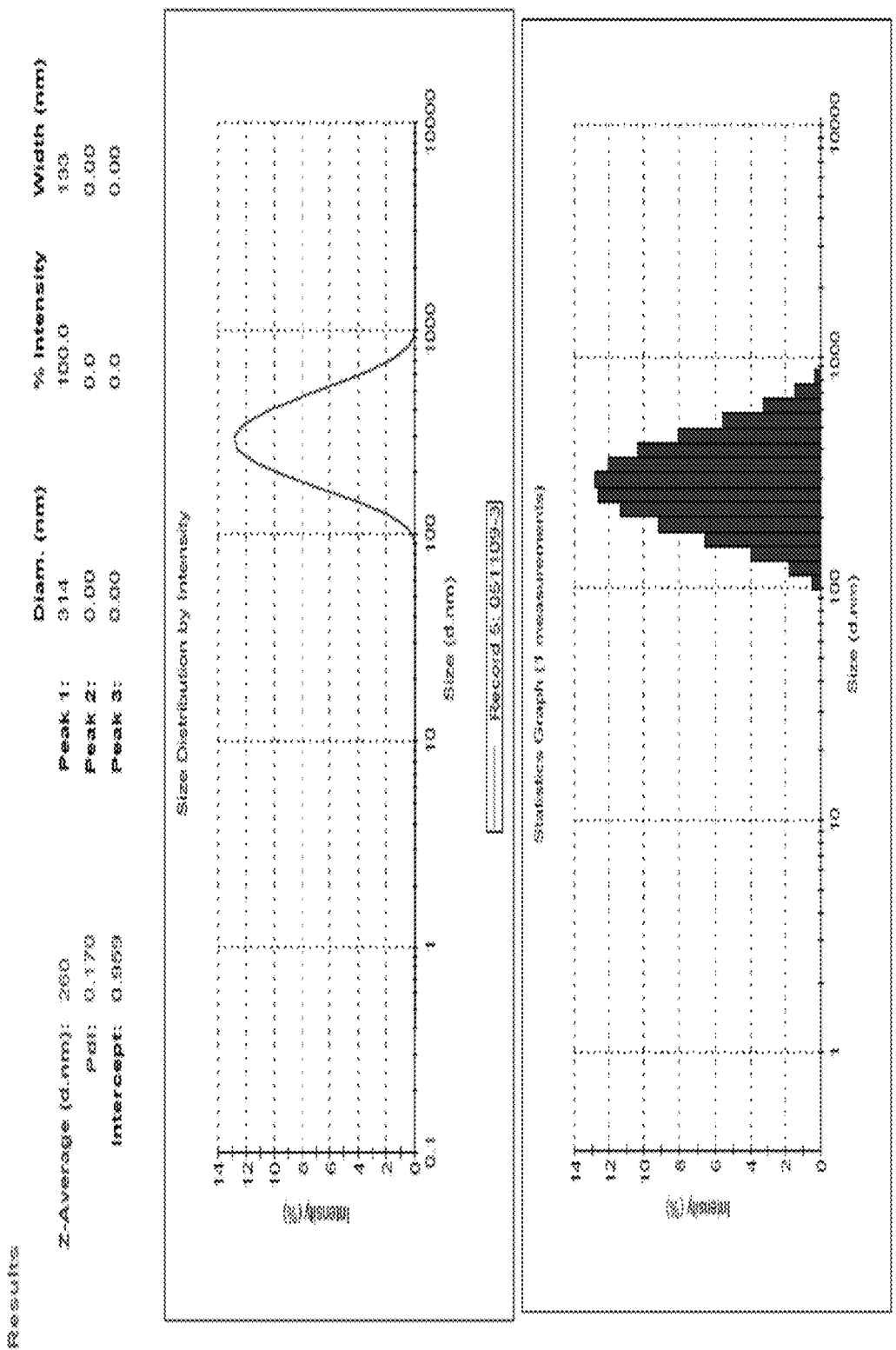

In FIGS. 3A and 3B, T3 nanoformulations produced by the gelation/conjugation process are further characterized. FIG. 3A shows a size measurement of T3 encapsulated PLGA-chitosan nanoparticles by DLS.

FIG. 3B shows a size measurement of T3 encapsulated PLGA-chitosan nanoparticles by DLS and including glutaraldehyde as a cross-linker. Other cross-linkers known in the art may be utilized.

Figure 4A:
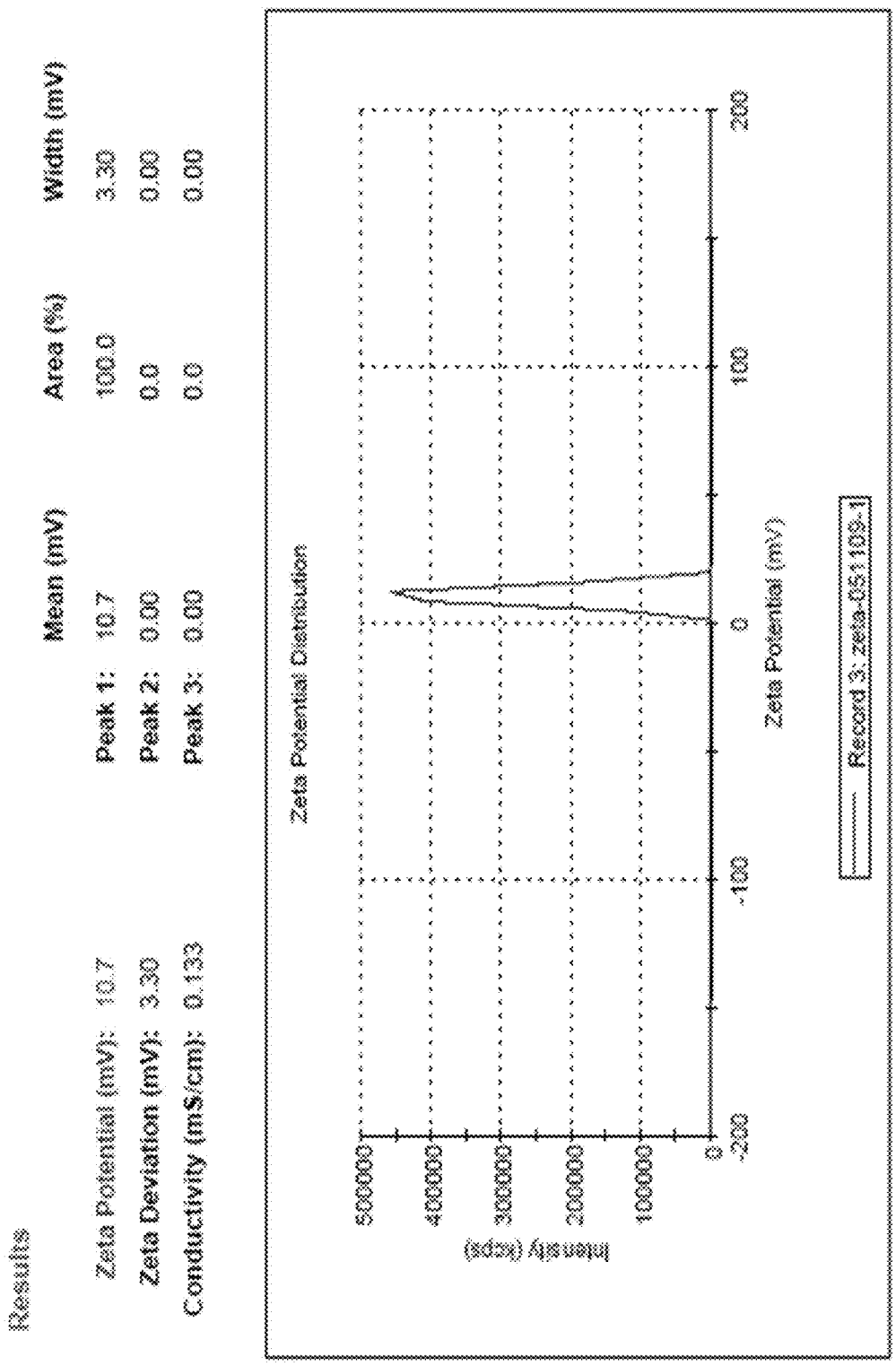
FIGS. 4A and 4B depict zeta potential measurements of T3-nanoparticles.
Figure 4B:
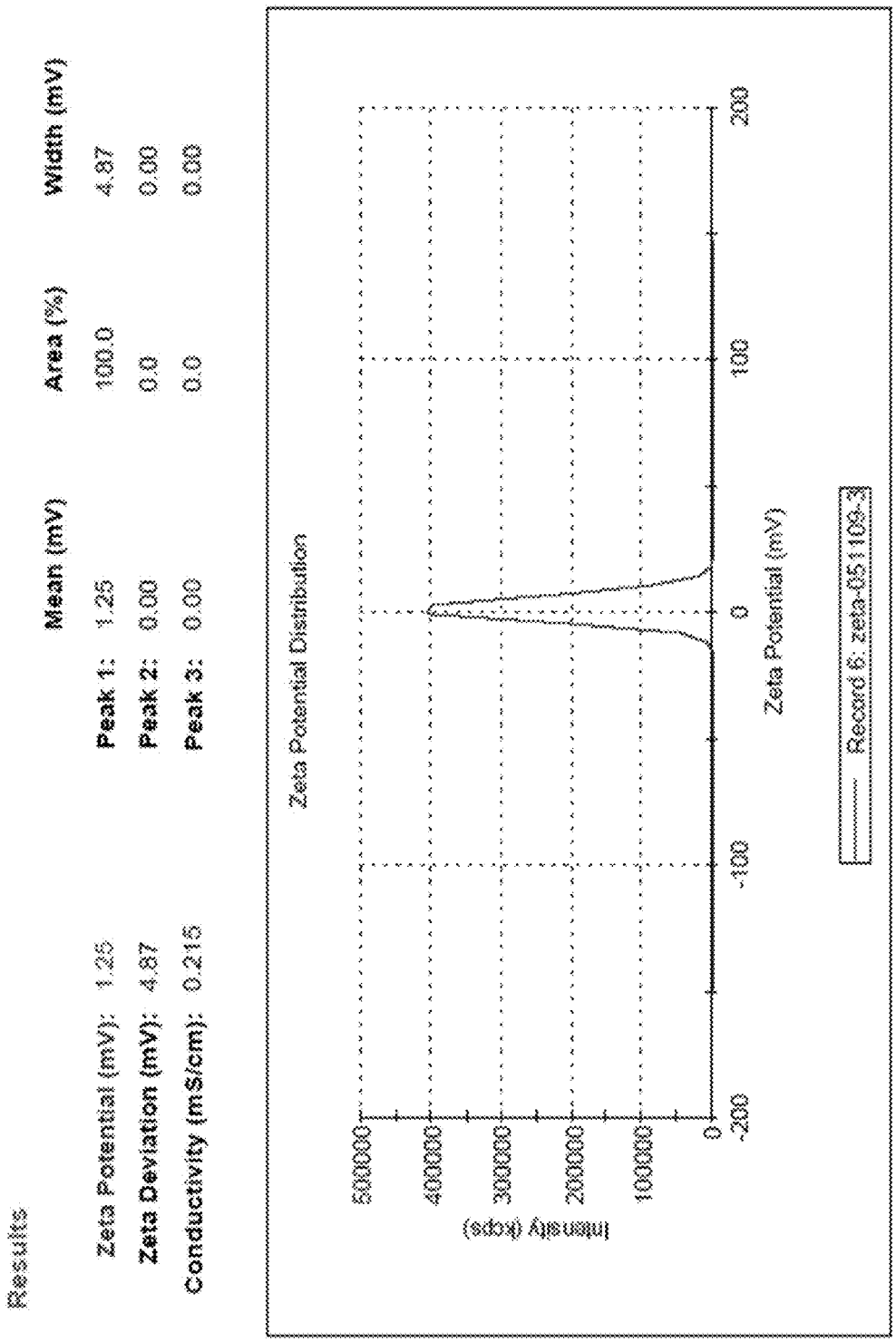

In FIG. 4A, a zeta potential measurement of T3 encapsulated PLGA-chitosan nanoparticles by DLS is shown. FIG. 4B shows a zeta potential measurement of T3 encapsulated PLGA-nanoparticles by DLS. In this case, glutaraldehyde was used as a cross-linker. The accompanying table shows that the zeta potential for the nanoparticles decreases when glutaraldehyde was used as a cross-linker.

Figure 5B:
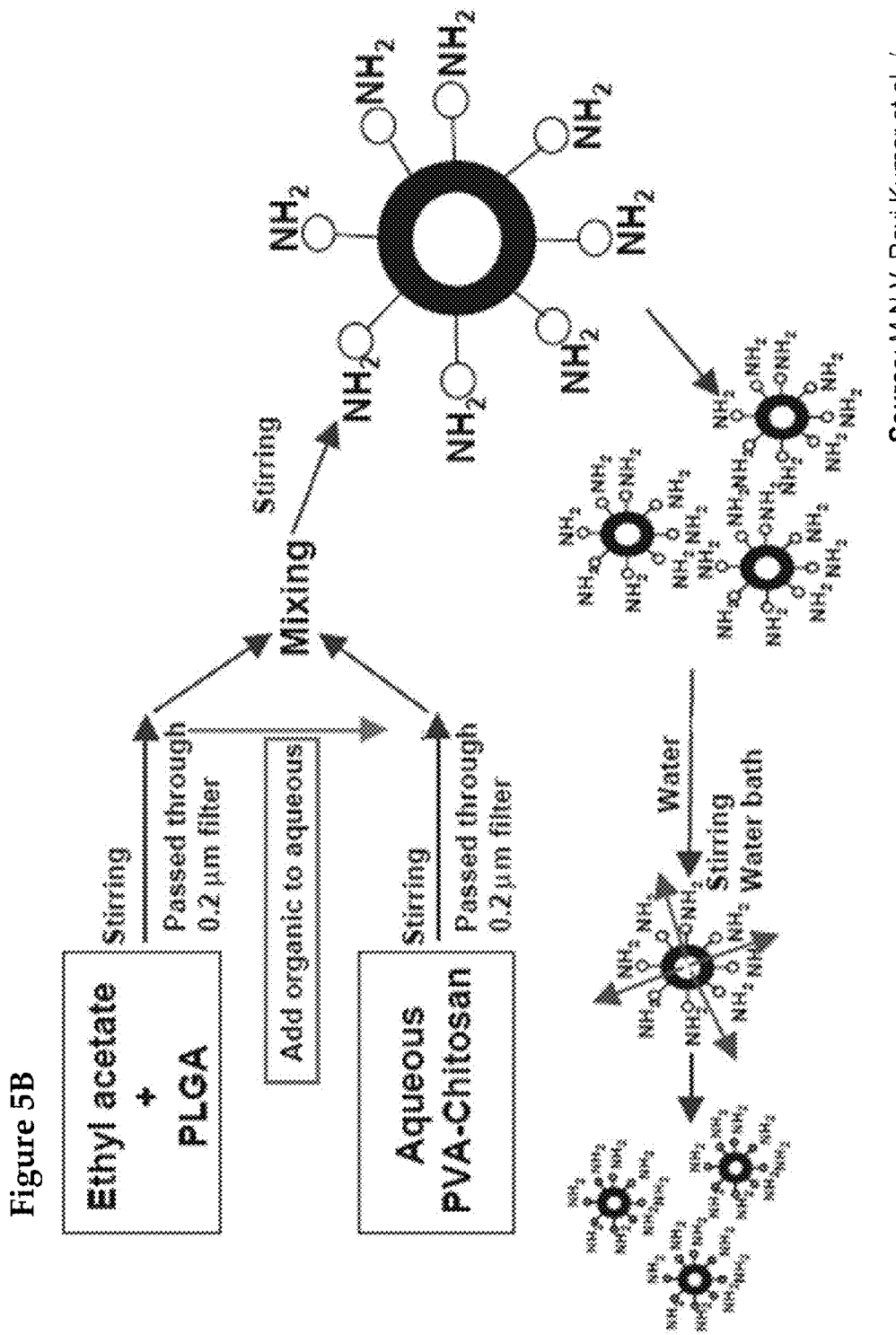

In FIG. 5, amounts of PLGA, chitosan, and PVA are shown. In addition, a relevant ph value, a particle size, a type of distribution, and a zeta potential are shown. A ratio of PLGA to chitosan is described. Also, a process of forming nanoparticles using PLGA and chitosan is shown.

Figure 6:
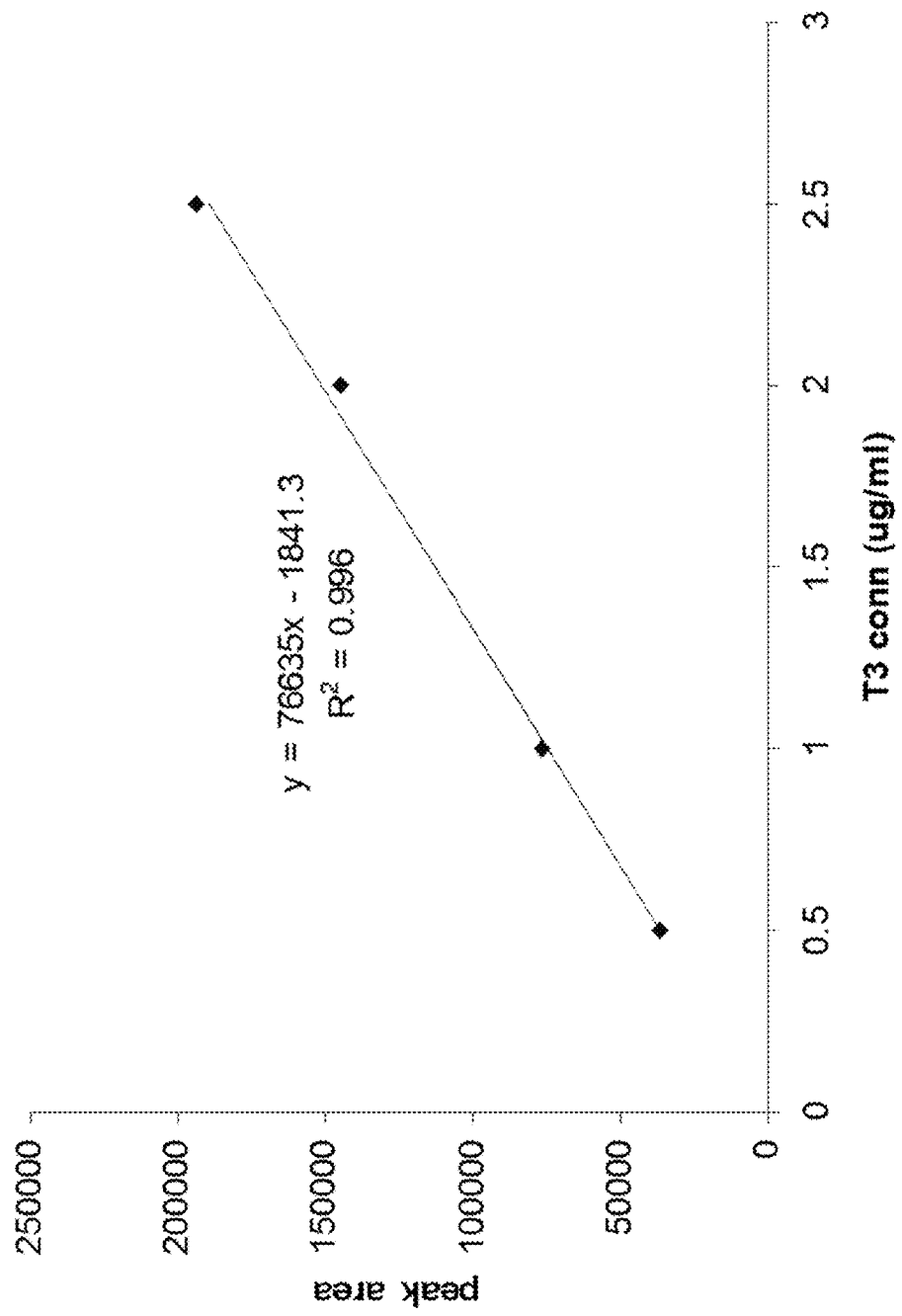
FIG. 6 depicts the kinetics of T3 nanoformulations.

In FIG. 6, kinetics of T3-nanoformulations are described. As the concentration of T3 increases, a peak area increases linearly.

Additionally, a loading level of T3 in a nanoparticle formulation measured by a HPLC method, are shown below as follows.

| Batch # | Treatment | T3 conn. (ug/ml) |
| --- | --- | --- |
| 051109-1 | add 1M NaOH, 2 hour | 82.18 |
| 051109-3 | add 1M NaOH, 2 hour | 19.89 |
| 051109-1 | directly diluted w/o NaOH | 87.26 |
| 051109-3 | directly diluted w/o NaOH | 19.77 |

An entrapment efficiency may also be measured. The entrapment efficiency may be calculated to be the total amount of T3 in the nanoparticles/initial concentration of T3 added to make the formulation×100. For example, the entrapment efficiency for a chitosan-PLGA-T3 nanoparticle is 82%. The entrapment efficiency for a chitosan-PLGA-T3 that is cross-linked with glutaraldehyde is only 20%. Thus, adding a cross-linker to the nanoparticles decreases the entrapment efficiency.

Figure 7A:
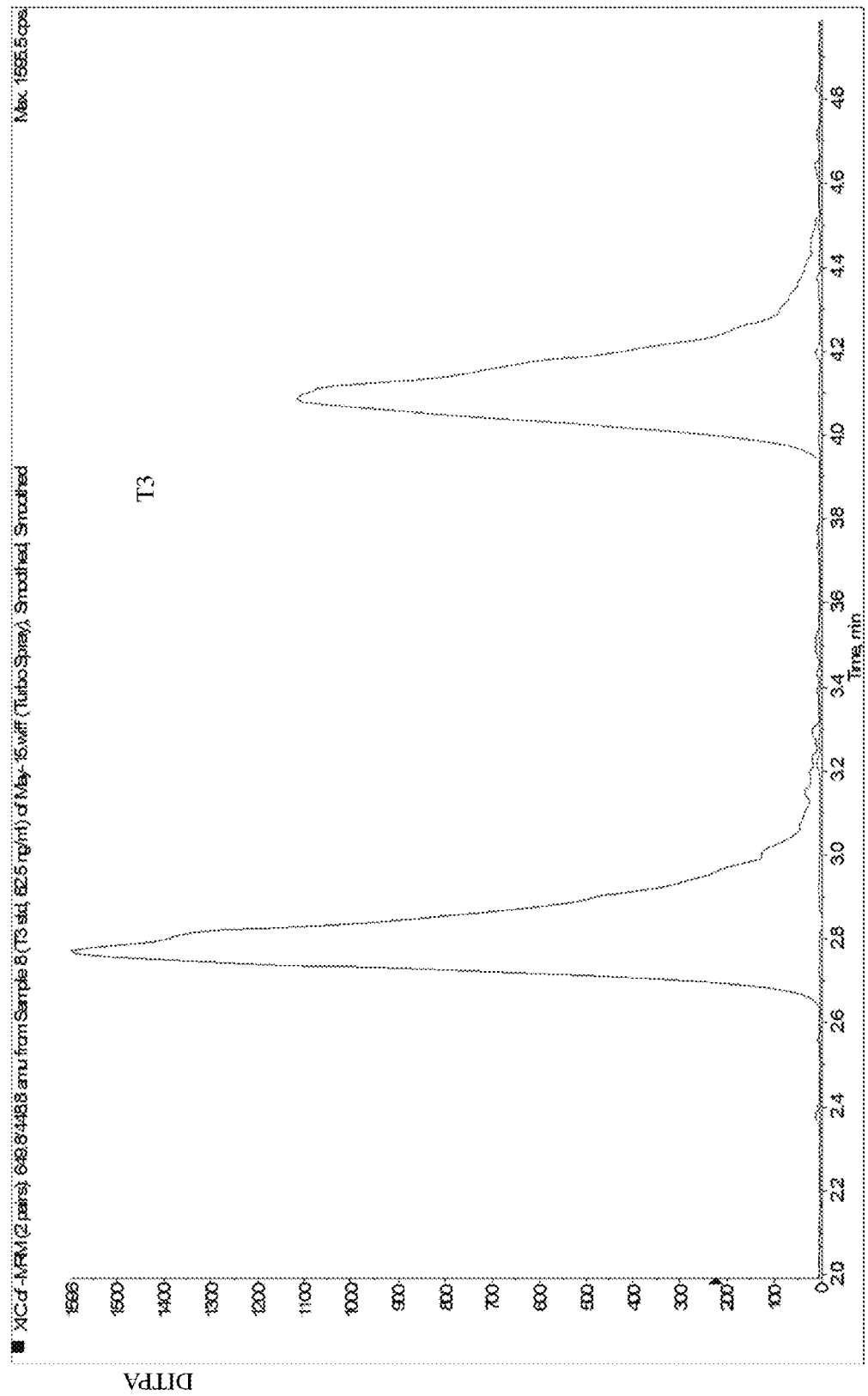
FIGS. 7A, 7B and 7C show other examples of kinetics of T3 nanoformulations.
Figure 7B:
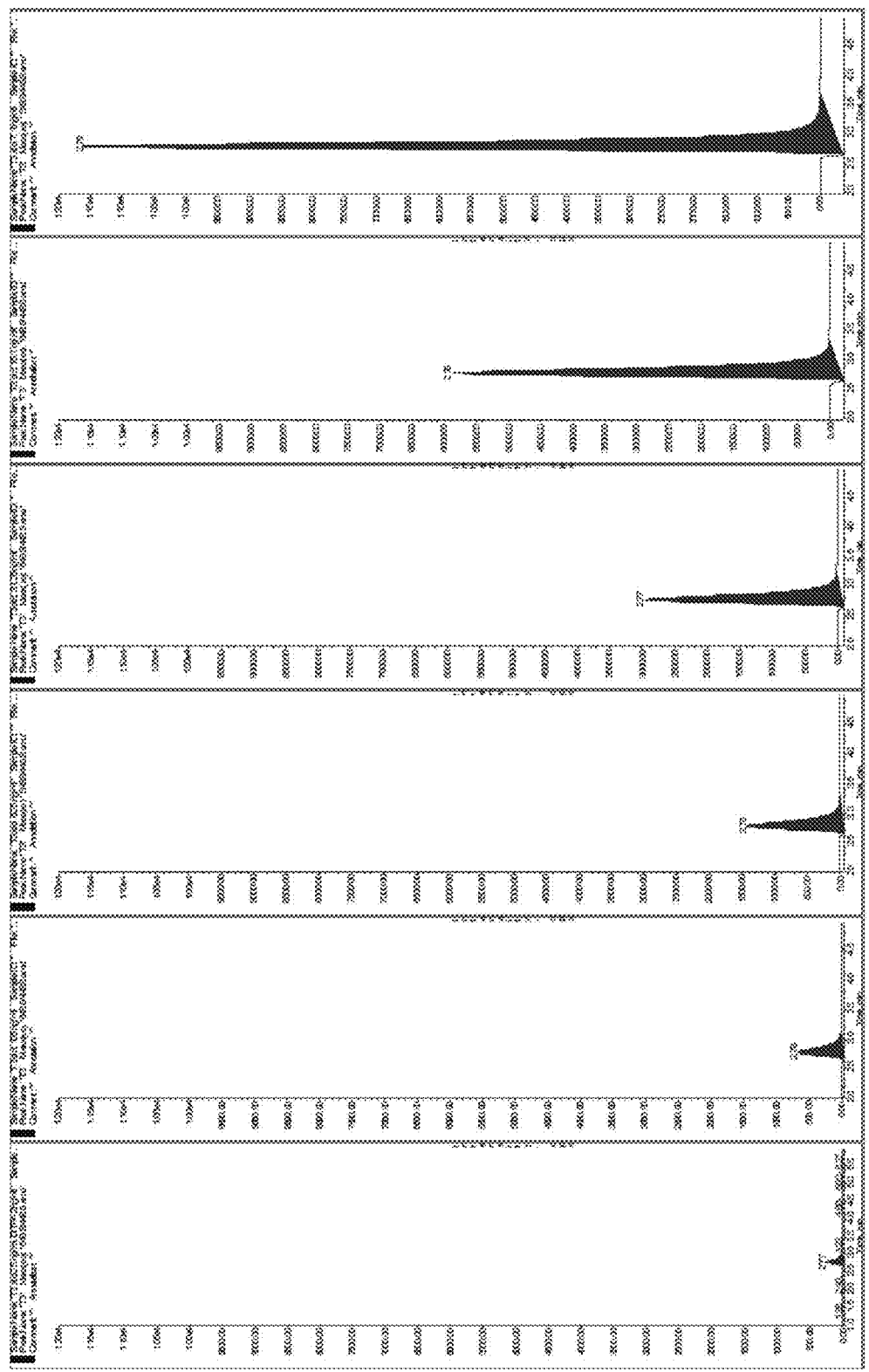
Figure 7C:
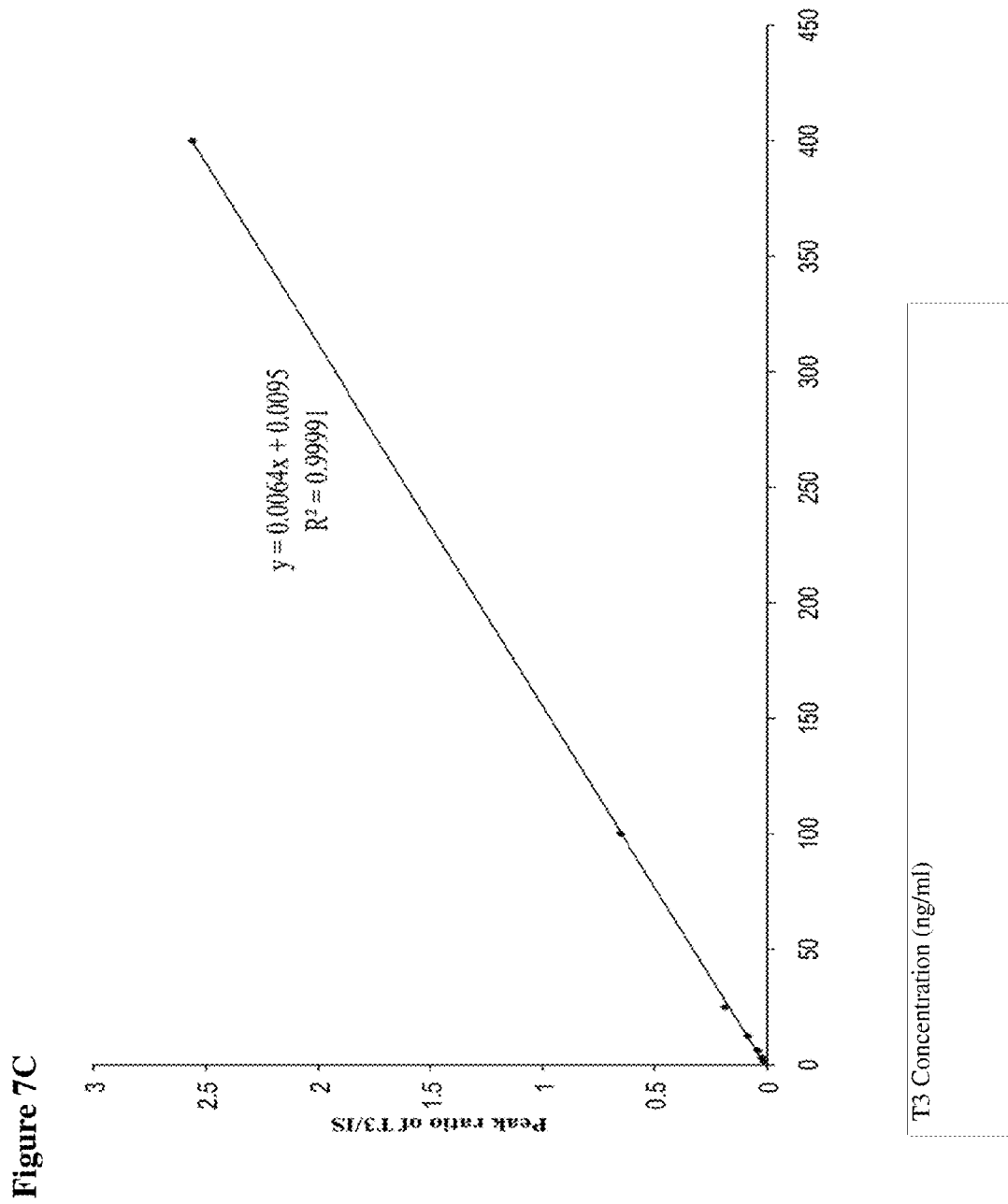

In FIGS. 7A-7C, other examples of kinetics of T3 nanoformulations are shown.

FIG. 7A depicts a typical MRM chromatogram of T3 and DIPTA assayed by the LC-MS/MS method. The conditions are described as follows:

LC-MS/MS Conditions for T3 Assay:
Column: C18, Waters Sunfire, 100 mm, at 40° C.;
Mobile phase are as follows: 70% 10 mM ammonium acetate, pH of 4.0;
T3: 649.8-448 m/z;
DITPA (as internal standard): 508.8-381.9 m/z;

A detect limit of T3: 37.5 pg in 15 μl may be detected;
An extraction efficiency of 85% may be achieved in one example.

FIG. 7B depicts a MRM chromatogram of a T3 standard assayed by LC-MS/MS method. FIG. 7C shows a calibration curve of T3 standard assayed by LC/MS/MS method. The calibration curve includes 1.56-400 ng/ml of a T3 standard.

In FIG. 8A, the figure shows that greater amount of T3 remained in the blood after time when a T3 nanoparticle comprising a PLGA-chitosan-glutaraldehyde nanoparticle was used. This T3-nanoparticle is administered intraperitoneally in mice. This result is in contrast with results from mice administered intraperioteneally with free T3. A lesser amount of T3 remains over time in mice administered with free T3 alone.

Figure 8B:
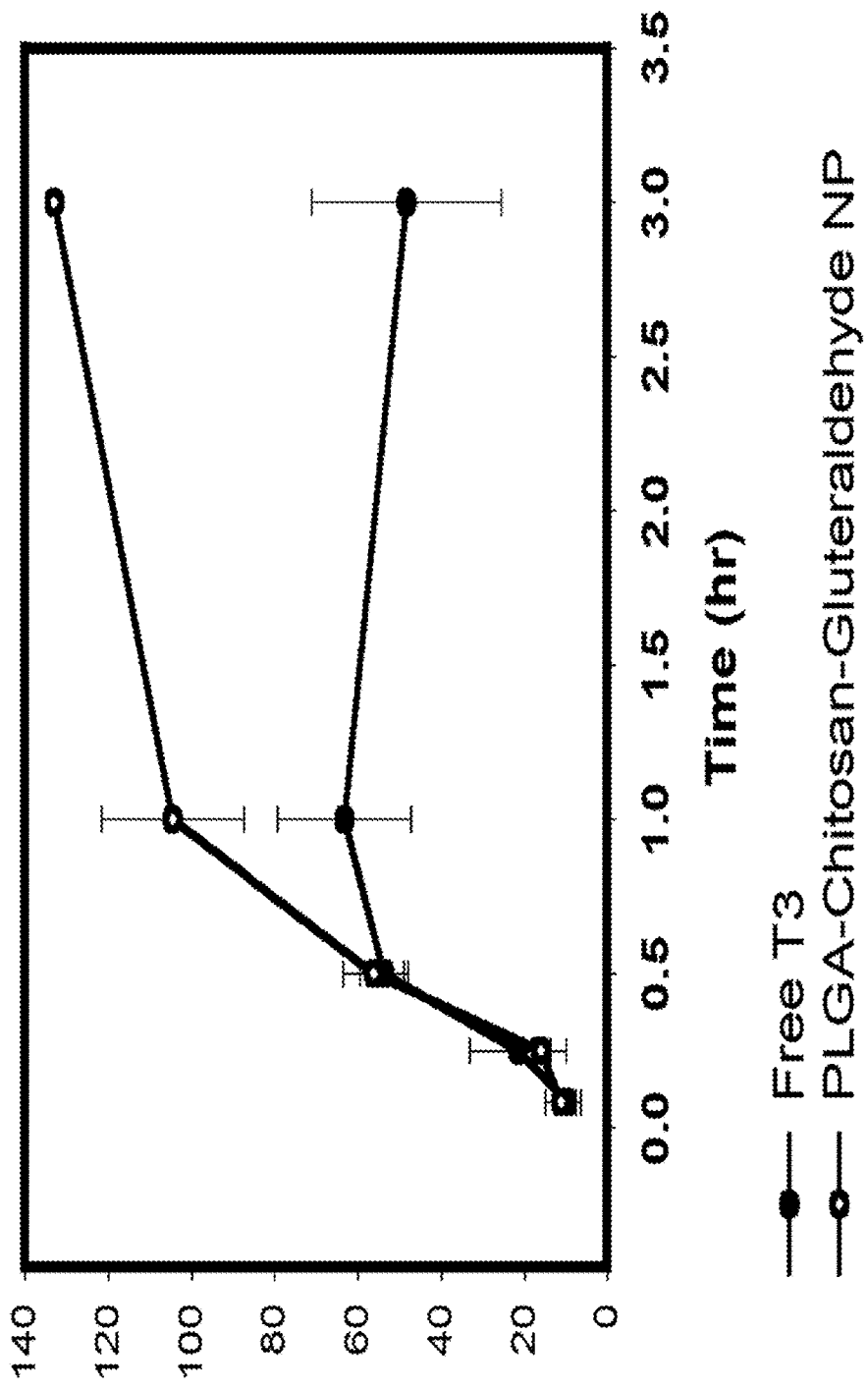
FIG. 8B shows another example of blood levels of T3 using T3 nanoparticles and T3 alone in mice.
Figure 9:
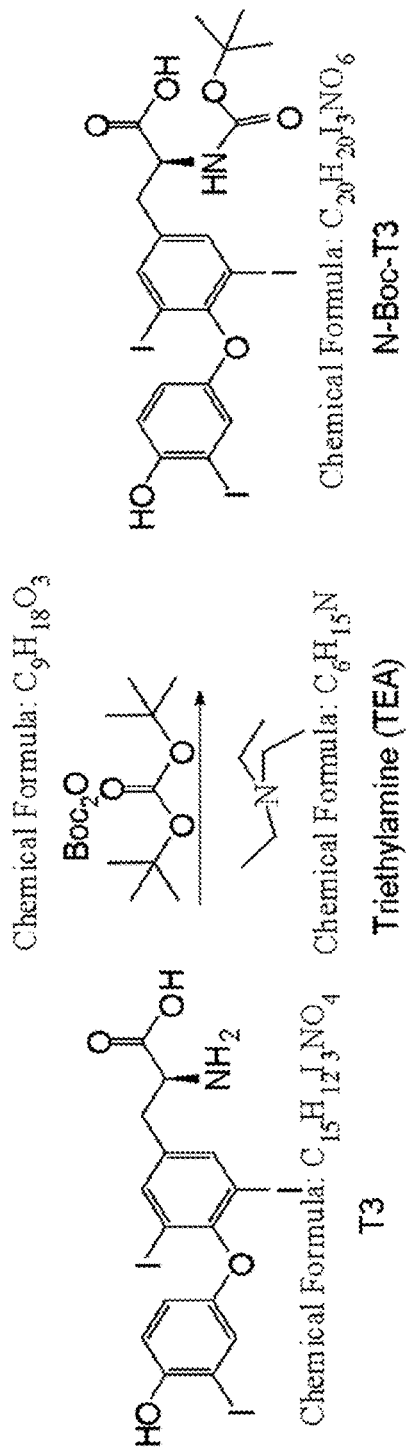
FIG. 9 shows one embodiment of the synthesis of amino-protected T3.
Figure 10:
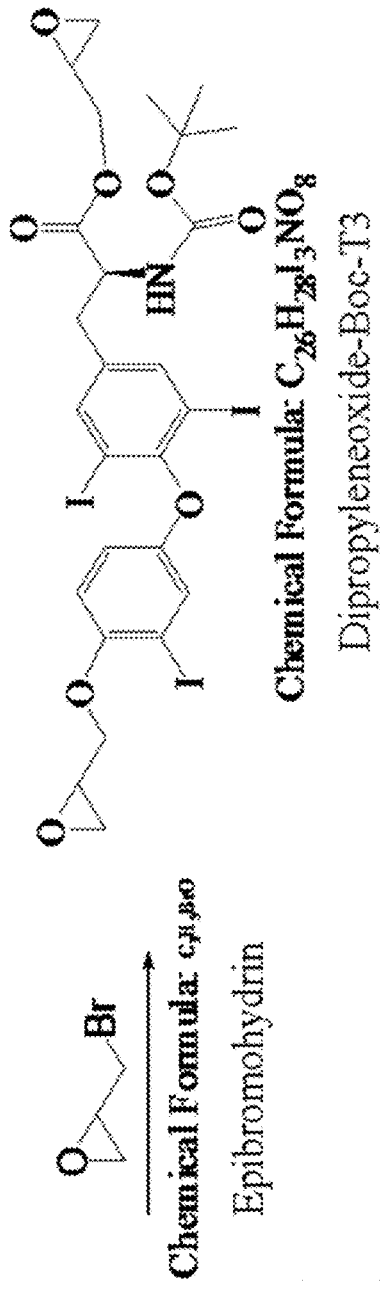
FIG. 10 shows one method in which T3 may thus be activated, for example using an epoxyalkyl of formula [CH2-O—CH]—[CH2]$_n$-X wherein n=1-5 and X is halogen, e.g. bromine.
Figure 11:
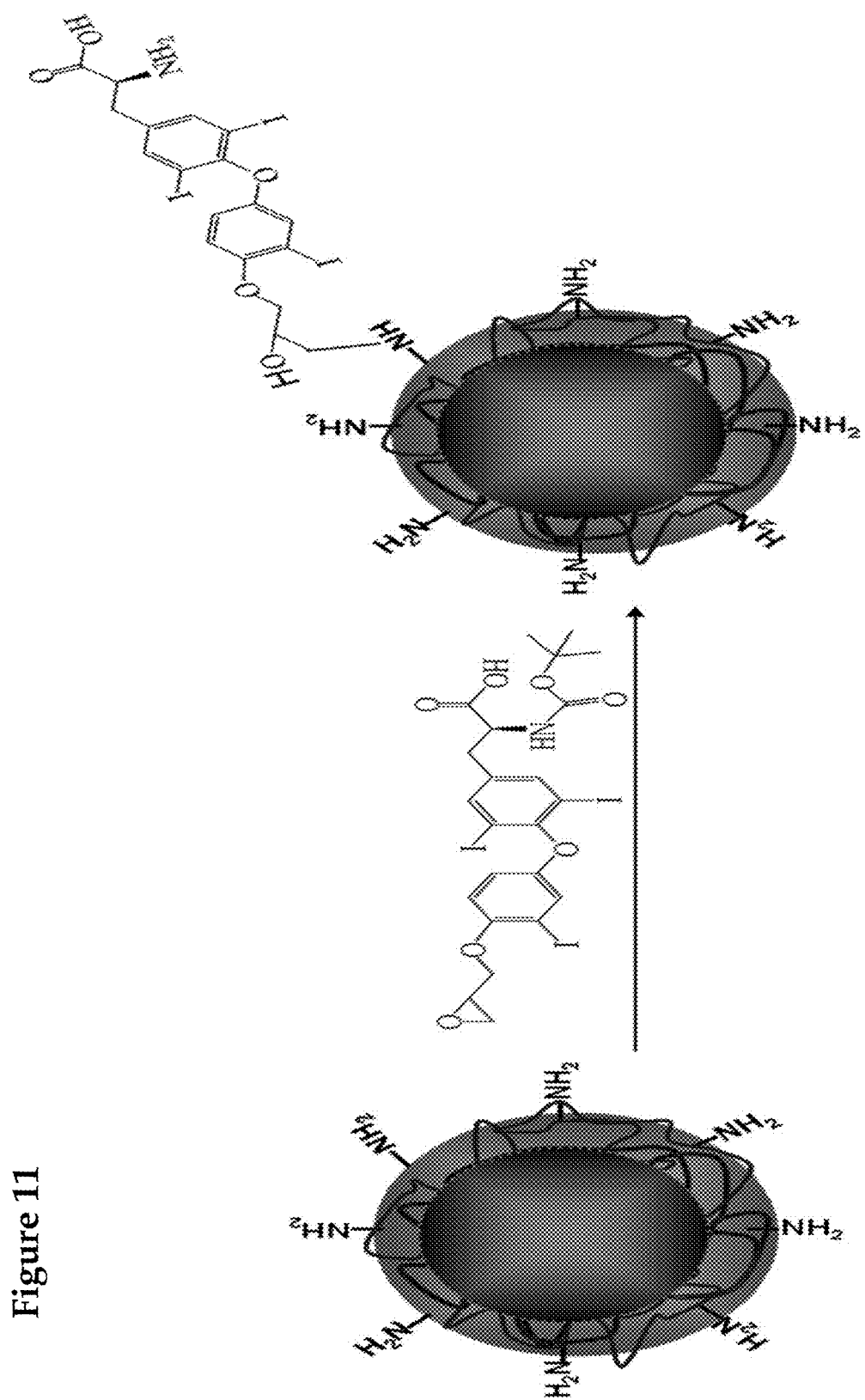
FIG. 11 shows one example of activated T3 attached to the bioabsorbable polymer, for example, T3 having an epoxy linker moiety and an amino-protecting group is reacted with a bioabsorbable polymer having amino groups, then deprotected to provide a nanoparticle covalently linked to T3.
Figure 12:
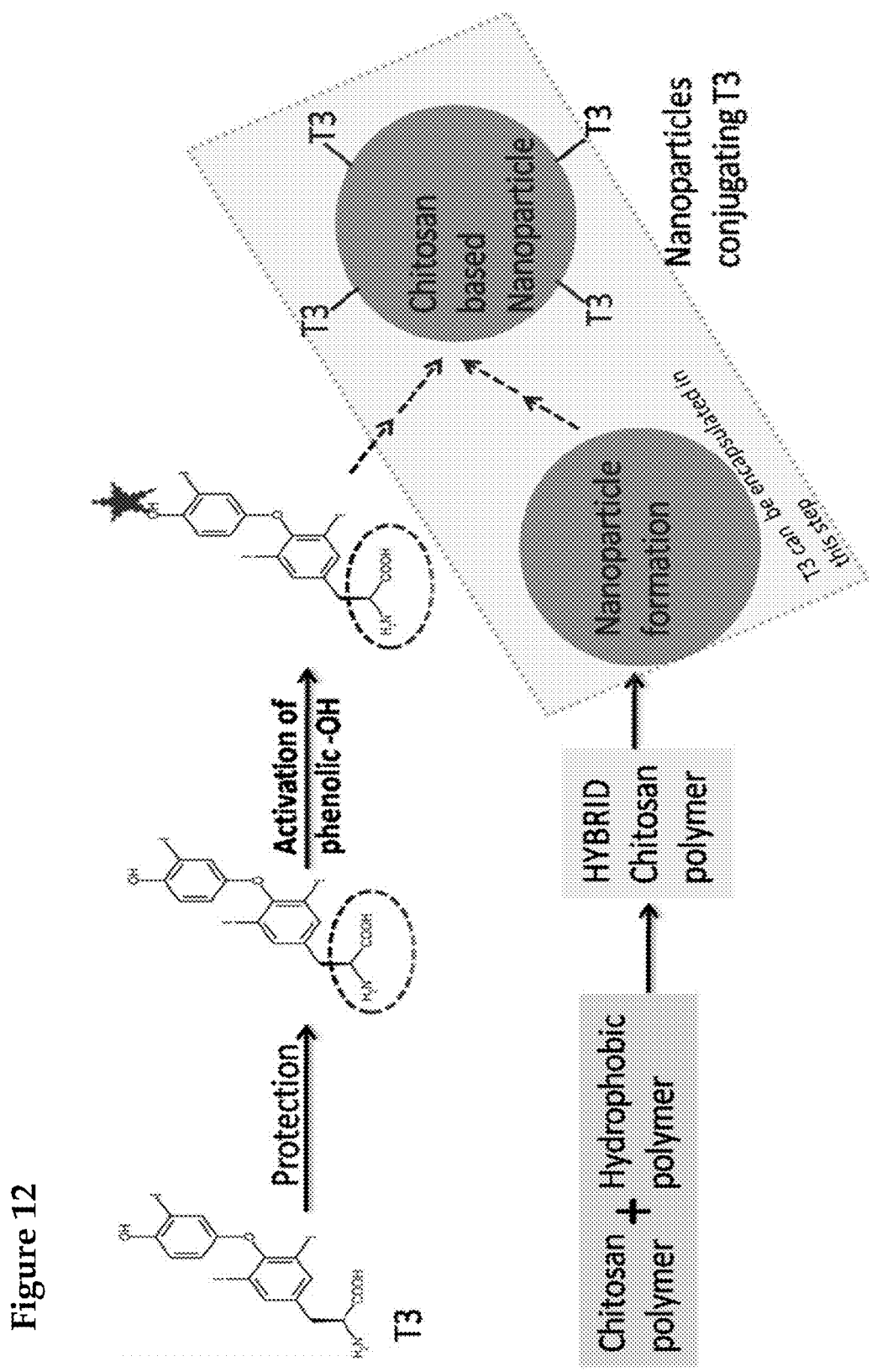
FIG. 12 shows one example of T3 attached to the bioabsorbable polymer.

In FIG. 8B, the intraperitoneal injection of a T3 nanoparticle comprising PLGA-chitosan-glutaraldehyde results in increased levels emerging in the bloodstream of mice.

By contrast, mice injected with free T3 have increased T3 blood levels which were followed by a subsequent leveling off.

Administration routes include, but not limited to intravenous, intracardiac, subcutaneous, intramuscular, orally and intrapulmonary.

The methods allow for delivery of T3 in a few minutes and provide sustained elevated serum concentration of T3 over time.

In one example of the method, the T3-nanoparticles may be lyophilized. The nanoparticles are stable with long shelf life. The T3-nanoparticles may be dispensable in physiological saline. The formulations may for example have a pH of 7.0-7.8, e.g., 7.4.

The size and surface charge of the T3-nanoparticles may be manipulated. For example, the following formulations of nanoparticles comprising T3 covalently bonded to chitosan are prepared:

| Chitosan based nanoparticle formulations | Size (nm) before conjugation to T3 | Size (nm) after conjugation to T3 | Zeta potential (mV) before conjugation to T3 | Zeta potential (mV) after conjugation to T3 |
|---|---|---|---|---|
| Formulation 1 | 256 | 279 | +5.73 | −2.42 |
| Formulation 2 | 264 | 303 | +18.2 | −0.833 |
| Formulation 3 | 252 | 239 | +15.2 | +4.51 |
| Formulation 4 | 336 | 294 | +21.1 | +11.7 |

The nanoparticles are shown to be stable over three months and do not show significant aggregation in solution.

Alternative combinations and variations of the examples provided will become apparent based on this disclosure. It is not possible to provide specific examples for all of the many possible combinations and variations of the embodiments described, but such combinations and variations may be claims that eventually issue.

The invention claimed is:

1. A formulation comprising T3 nanoparticles, wherein the T3 nanoparticle comprises T3 encapsulated or immobilized on a bioabsorbable polymer, wherein the bioabsorbable polymer is chitosan and wherein the formulation comprises poly (lactic-co-glycolic acid) (PLGA) wherein the polymer comprises chitosan crosslinked using glutaraldehyde.

2. The formulation of claim 1 wherein the polymer comprises chitosan linked to bile acids.

3. The formulation of claim 1 wherein the polymer comprises chitosan linked to PLGA.

4. The formulation claim 1 wherein the nanoparticles have an average diameter of 50-1000 nm.

5. The formulation of claim 1 wherein the nanoparticles have a zeta potential of 10-100 mV.

6. The formulation of claim 1 wherein the nanoparticle comprises a second pharmacologically active ingredient.

7. The formulation of claim 1 comprising T3 which is not covalently bound to the polymer.

8. The formulation of claim 1 comprising T3 which is covalently bound to the polymer.

9. The formulation of claim 1 comprising both T3 which is not covalently bound to the polymer and T3 which is covalently bound to the polymer.

10. A composition according to claim 1 comprising T3 covalently linked to chitosan.

11. The composition of claim 10 wherein the linkage is between the amino groups on the chitosan and the phenolic hydroxy on the T3.

12. A method of making a T3 nanoparticle according to claim 1, comprising:
   providing PLGA and T3;
   immersing the PLGA and T3 in a 1% solution including chitosan;
   stirring and sonicating; and
   performing a dialysis step, to yield the T3 nanoparticle further comprising a step of crosslinking a chitosan layer formed in the T3-nanoparticle with a cross-linker wherein the step of crosslinking utilizes glutaraldehyde as the cross-linker.

13. A method for treating a cardiac condition, comprising administering an effective amount of a formulation of claim 1 to a patient in need thereof.

14. The method of claim 13, wherein the cardiac condition is cardiac arrest.

15. The method of claim 13 wherein the cardiac condition is pulseless electrical activity.

* * * * *